United States Patent [19]

Sgro

[11] Patent Number: 5,496,365
[45] Date of Patent: Mar. 5, 1996

[54] AUTOEXPANDABLE VASCULAR ENDOPROSTHESIS

[76] Inventor: Jean-Claude Sgro, 42 Cours du General de Gaulle, 21000 Dijon, France

[21] Appl. No.: 275,913

[22] Filed: Jul. 15, 1994

Related U.S. Application Data

[63] Continuation of Ser. No. 907,690, Jul. 2, 1992, abandoned.

[51] Int. Cl.⁶ .............................. A61F 2/06; A61F 2/02; A61M 29/02
[52] U.S. Cl. .............................. 623/1; 623/11; 606/191; 606/194
[58] Field of Search .................... 606/191–200, 606/158, 157; 623/1, 11, 12; 600/36

[56] References Cited

U.S. PATENT DOCUMENTS

| | | | |
|---|---|---|---|
| 4,580,560 | 4/1986 | Gianturco | 604/96 |
| 4,617,932 | 10/1986 | Kornberg | 623/1 |
| 4,699,611 | 10/1987 | Bowden | 604/51 |
| 4,732,152 | 3/1988 | Wallsten et al. | 623/1 |
| 4,733,665 | 3/1988 | Palmaz | 623/1 |
| 4,762,128 | 8/1988 | Rosenbluth | 604/96 |
| 4,990,151 | 2/1991 | Wallsten | 606/198 |
| 5,071,407 | 12/1991 | Termin et al. | 606/194 |

FOREIGN PATENT DOCUMENTS

| | | |
|---|---|---|
| 274846 | 7/1988 | European Pat. Off. . |
| 364787 | 4/1990 | European Pat. Off. . |
| 0423916 | 4/1991 | European Pat. Off. ........... 623/1 |
| 2671280 | 7/1992 | France . |
| 3417738 | 11/1985 | Germany . |
| 8812719 | 12/1989 | Germany . |
| 9010130 | 10/1990 | Germany . |

*Primary Examiner*—Debra S. Brittingham

[57] ABSTRACT

A vascular endoprosthesis intended to maintain the walls of anatomic channels. The endoprosthesis is formed by a combination of longitudinal juxtaposed unitary assemblies (1) having flexible, elastic longitudinal ribs (3, 4, 5) connected to each other by transverse strands (2) which are also flexible and elastic and are fastened on an intermediate rib (3) in such a manner as to form "V's" with the intermediate rib (3). The combination forms a herringbone structure, the assembly of which by juxtaposition with other such assemblies forms an openwork cylinder (53).

15 Claims, 4 Drawing Sheets

5,496,365

AUTOEXPANDABLE VASCULAR ENDOPROSTHESIS

This is a continuation of application Ser. No. 07/907,690 filed on Jul. 2, 1992, now abandoned

BACKGROUND OF THE INVENTION

1. Field of the Invention

The present invention concerns the medical-surgical field, in particular arterial pathology, but also more generally the pathology of other anatomical canals, such as the venous, biliary and urinary canals, its object being an autoexpandable vascular endoprosthesis of permanent elasticity and only slight shortening upon insertion into the canals, as well as a device for the use thereof.

2. Description of the Related Art

In the present state of the art, endolumenal arterial prostheses already exist, referred to in the international medical literature by the English expression "stent".

These prostheses are of two types:
 ones of nonelastic metallic material expandable from the inside towards the outside under the effect of an inflatable balloon;
 others of elastic metallic material formed of metal meshes; they are introduced stretched into the lumen of the vessel and their diameter increases when the longitudinal extension is relaxed.

These prostheses have various drawbacks:
 those of the first type must be carefully adjusted on a balloon since, once expanded, they can no longer be withdrawn;
 those of the second type do not have this drawback, but the structure of their meshes requires substantial longitudinal extension in order to reduce their diameter, a condition indispensable in order to be able to introduce them into a vessel; once introduced, their retraction within the vessel is also very substantial, resulting in difficulties in adjustment and in rubbing on the walls of the vessel over a length of several centimeters.

SUMMARY OF THE INVENTION

In order to avoid the necessity of too substantial an extension and rubbing on the walls of the vessel, the endoprosthesis of the invention is constructed in accordance with a special geometry which establishes its originality.

The endoprosthesis of the invention is characterized essentially by the fact that it is as a whole cylindrical and is based on an assembly of longitudinal ribs made of elastic solid materials to which there are firmly attached, arranged transversely at a given angle, strands which are also elastic and which form regular ladders between two adjacent ribs, the different ladders which are connected together longitudinally forming an extensively openwork, open-ended cylinder.

The endoprosthesis of the invention is formed of a combination of unitary elements comprising three ping. From the two outer ribs, transverse elastic strands contact the intermediate rib at a convergent angle, the transverse strands being in the form of an open "V", forming a "herringbone" structure with the intermediary rib.

When longitudinal tractions in opposite directions are exerted on the outer ribs and the intermediate rib, the "V's" close, bringing the outer ribs towards the intermediate rib.

The longitudinal displacement of the ribs is very slight in order to obtain the closing of the "V's" and the bringing together of the ribs.

The tractions exerted on the entire prosthesis by pulling the neighboring longitudinal ribs in opposite direction cause a decrease in the diameter of the cylinder, bringing the ribs together. Thus, the prothesis can change from a generally openwork cylindrical tube of a given radius to a tube of smaller radius by a small extension and a slight longitudinal displacement of the ribs.

since the structure of the "V" strands is elastic, the tube is autoexpandable and resumes its initial shape when the traction is relaxed.

The diameter of the prosthesis of the invention is a function of the anatomic canal to be fitted, and it may vary from a few millimeters to a few centimeters, while its length is also adapted in accordance with the requirements.

The present invention comprises the prosthesis which has just been described, but also its system of application, which is formed of two concentric cylinders of small diameter, the distal end of the endoprosthesis being fastened to the end of the cylinder of smaller diameter and its proximal end to the end of the cylinder of larger diameter.

By pulling on the cylinder of larger diameter, the endoprosthesis is stretched out in order to reduce its diameter. Thus stretched, it can be brought to the desired place; it is then relaxed so that it pushes against the walls of the artery. It can be stretched again for displacing it, if necessary, as long as it is not detached from the application system. During its introduction and displacement in the anatomic canal, the assembly can be covered by a third cylinder which protects the prosthesis and avoids any catching on the walls of the canal.

The endoprosthesis of the invention is made of a material which is capable of retaining permanent elasticity so as to be able to spread the walls, for instance, of an artery, and to stay in place despite the circulation of the blood flow and possible enlargements of the diameter of the vessels due to their own elasticity and alternate variations in pressure.

The material employed may be an elastic metal, an alloy or a plastic which can retain its elasticity with time.

The endoprosthesis of the invention can furthermore be covered either by a biological coating or by a protective substance offering little adherence for the blood, bile or other liquid which is to flow through it.

The prosthesis of the invention, as a result of its geometry, has the advantage of being elastic, autoexpandable with slight shortening, and collapsible as long as it is not disconnected from its application system.

The present invention will be better understood from a reading of the following description of certain of its embodiments, illustrated in the accompanying drawings, it being understood that this description is not limitative of the invention.

BRIEF DESCRIPTION OF THE DRAWINGS

In the accompanying drawing:

FIG. 9c showing the position of the ribs when the prosthesis has been placed in an artery;

DESCRIPTION OF THE PREFERRED EMBODIMENTS

Figure 1:
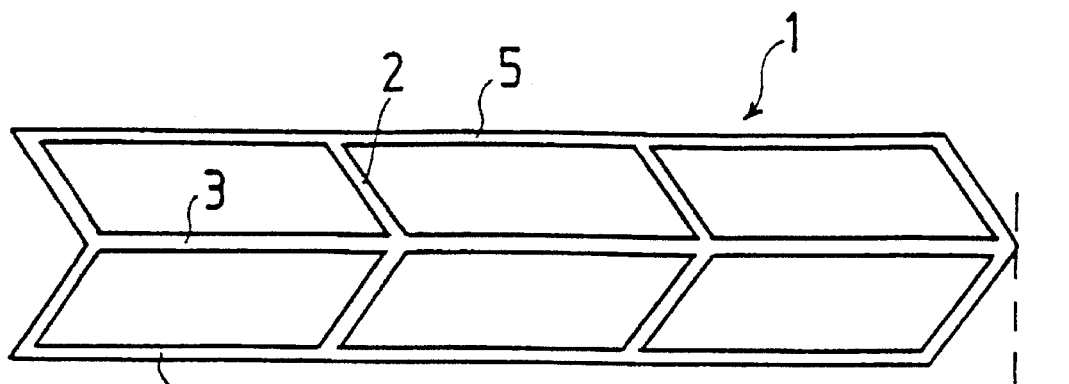
FIG. 1 is a partial view of a unitary assembly comprised in the endoprosthesis according to the invention.
Figure 2:
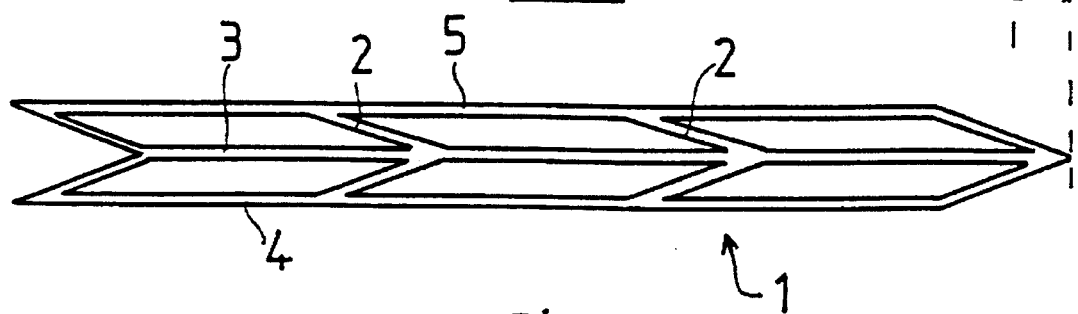
FIG. 2 shows the same assembly after extension.

Referring first of all to FIGS. 1 and 2, it is seen that a unitary assembly 1 of the endoprosthesis according to an embodiment of the invention is formed of two external ribs 4 and 5 connected to an intermediate rib 3 by means of strands 2 arranged in V shape in the same direction, in a herringbone pattern. As seen in FIGS. 1 and 2, each pair of adjacent ribs and each pair of adjacent strands forms a parallelogram-shaped opening in the assembly.

In order to stretch this unitary assembly 1, it is necessary to pull the neighboring longitudinal ribs in opposite directions, that is to say the ribs 4 and 5 in a direction opposite the rib 3. The "V's" being all arranged in the same direction, the elongation is minimal when the element 1 is stretched. As seen in FIGS. 1 and 2, each individual V-shape and the assembly as a whole extend only a distance "d" in response to a given traction. This is contrary to the conventional mesh prostheses, the meshes of which form diamonds which are elongated upon traction, each elongation adding on to that of the adjacent diamond, so that one finally obtains a very substantial total elongation.

FIG. 2 shows the assembly 1 flattened under the effect of traction in opposite directions of the outer ribs 4 and 5 and the intermediate rib 3.

Figure 3:
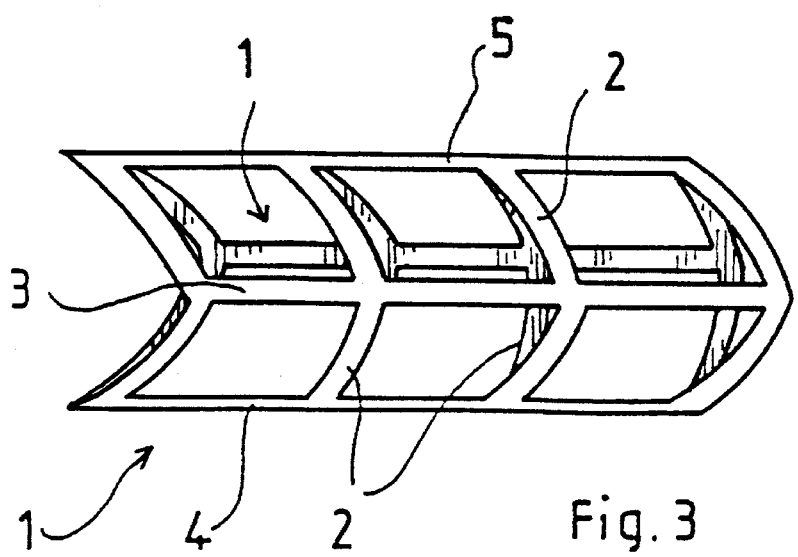
FIGS. 3, 4 and 5 show endoprostheses obtained by the longitudinal juxtaposing of two, three or four unitary assemblies of FIG. 1, respectively.
Figure 4:
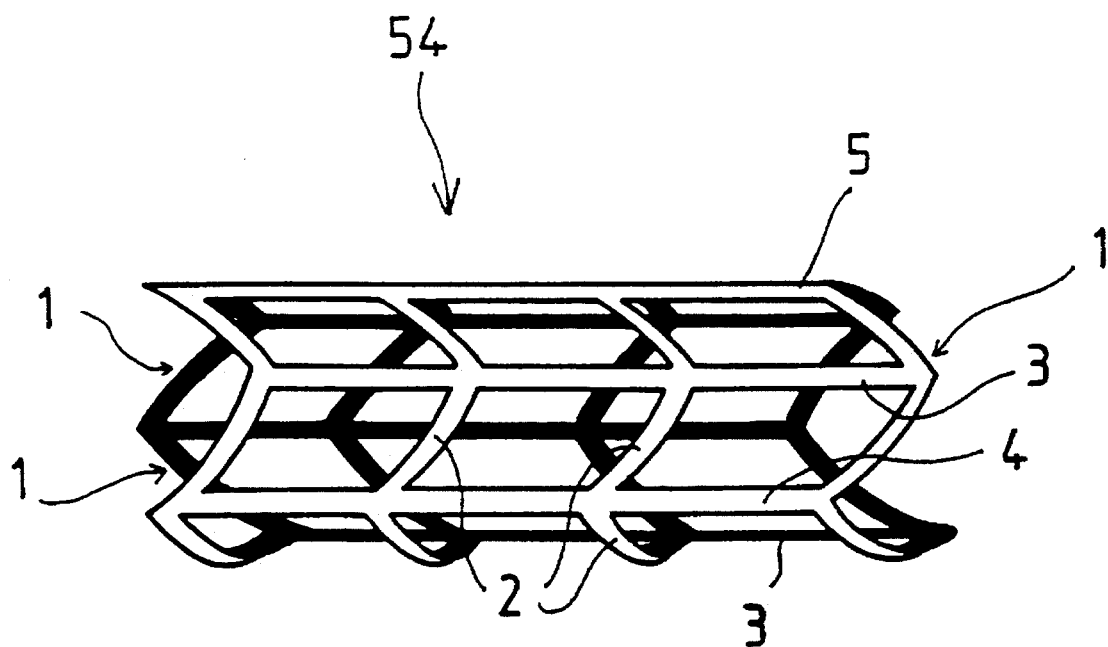
Figure 5:
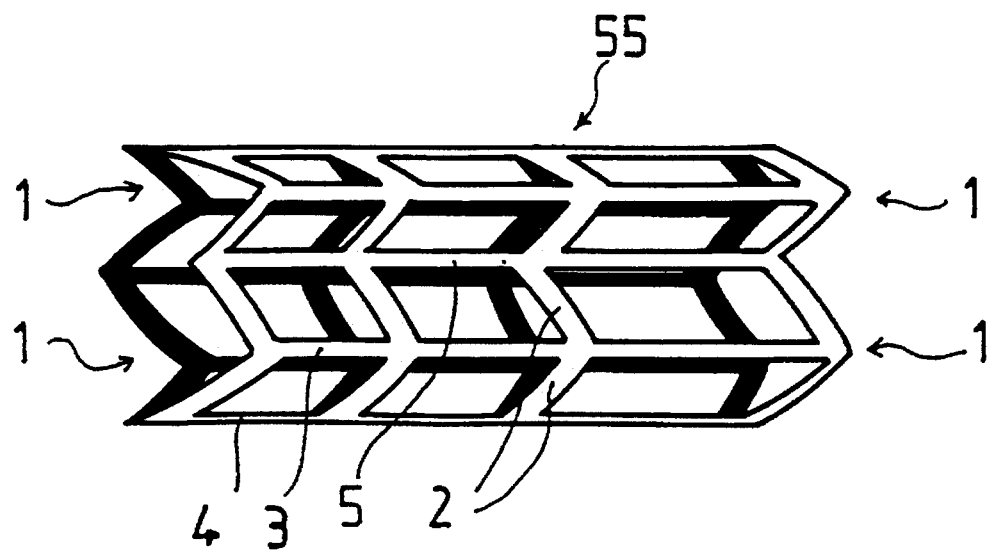
Figure 9A:
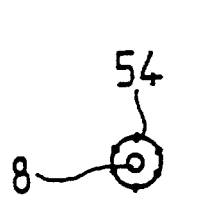
FIGS. 9a, 9b and 9c are cross sections showing, before, during and after extension, and the position of the main ribs around the central axis of the application system.
Figure 9B:
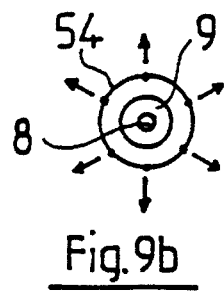
Figure 9C:
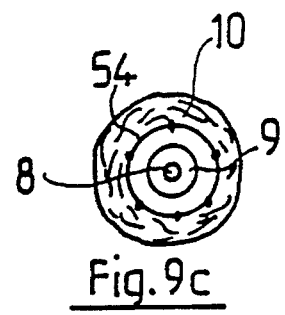
Figure 10:
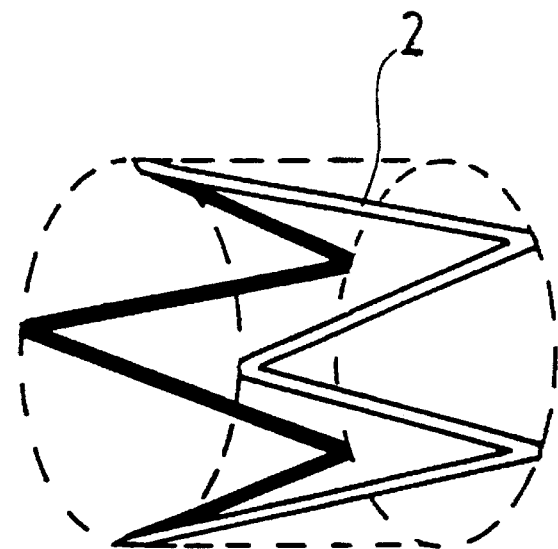
FIG. 10 shows the ring formed by the transverse strands of the unitary assembly of FIG. 1.

Referring to FIGS. 3, 4 and 5, it is seen that by the assembling by longitudinal juxtaposition of 2, 3 or 4 unitary assemblies 1 it is possible to obtain elastic cylinders 53, 54, 55, traction on the adjacent ribs of which in opposite direction, makes it possible to reduce the diameter. The relaxation of the traction in a vessel of adapted caliber permits the endoprosthesis to remain firmly applied to its walls (see FIG. 9c) as a result of the elasticity of its strands. The uniform shape of the strands as a "V" permits a uniform circular elasticity due to the spreading force which they apply at their base, the assembly of the contiguous V's forming a regular ring the inner lumen of which is circular and uniform (see FIG. 10).

Figure 6:
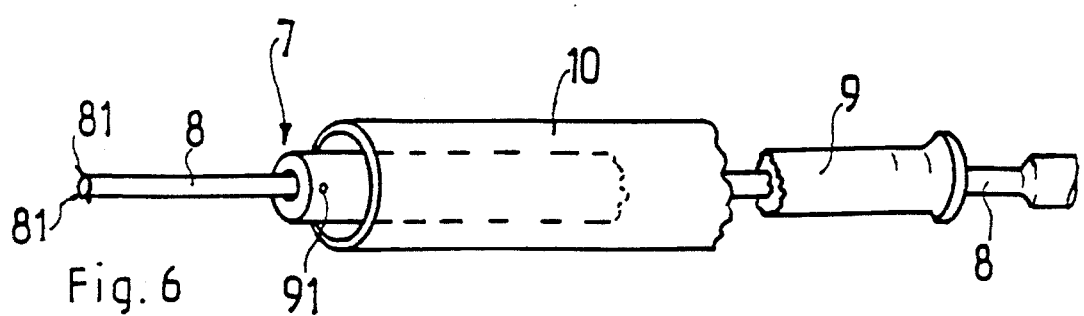
FIG. 6 is a perspective view, partially broken away, of a system for the application of the prosthesis of the invention.
Figure 7:
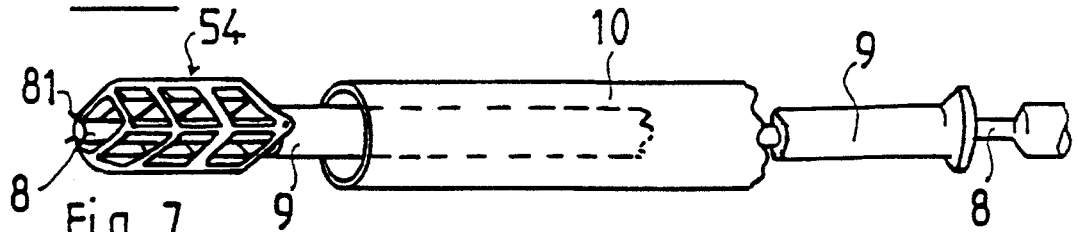
FIG. 7 is a perspective view, partially broken away, of the application system of FIG. 6 with the endoprosthesis fastened on it.
Figure 8:
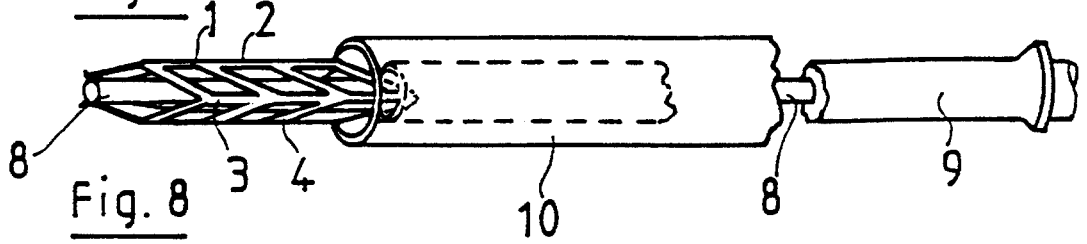
FIG. 8 is a perspective view, partially broken away, of the same system of application with the endoprosthesis stretched.

For introduction, for instance, into a blood vessel the walls of which it is desired to keep apart, the endoprosthesis is placed on the application system 7, shown in FIGS. 6 to 8, which makes it possible to bring it to the desired place.

The application device 7 is formed of two concentric cylinders 8 and 9 which slide one on the other. The distal part of the inner cylinder 8 is provided witch spurs 81 on which there is fastened one end of the endoprosthesis 54, its other end being fastened to the outer cylinder 9, which is provided on its distal end with the same number of spurs 91.

By sliding the outer cylinder 9 on the inner cylinder 8, the endoprosthesis 54 is stretched, reducing its diameter. Upon relaxing the tension, the increase in the diameter of the endoprostheses enables it to fasten itself on the wall of the vessel 10 (see FIG. 9c), which the endoprosthesis maintains open.

Figure 11:
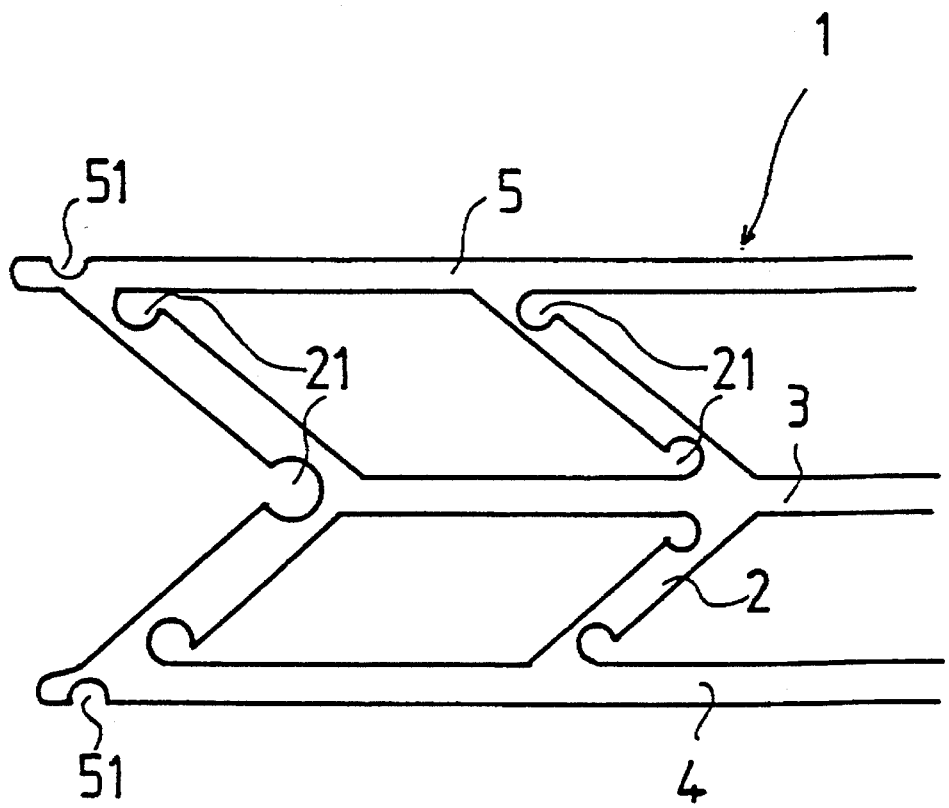
FIG. 11 is a detailed view of part of an assembly corresponding to FIG. 1, showing strands and ribs of the endoprosthesis according to another embodiment of the invention.

The fastening of the endoprosthesis 54 on the application device 7 is effected at the level of orifices arranged at its ends and formed by the bringing together, upon the assembling of the unitary assemblies 1, of notches 51 provided at the ends of the unitary assemblies 1, as can be noted from FIG. 11.

In this FIG. 11, it is seen that the transverse strands 2 can be provided with notches 21 in the vicinity of their ends so as to facilitate the closing of the angles which they form with the ribs 3, 4 and 5 upon the putting in place of the endoprosthesis.

I claim:

1. An autoexpandable vascular endoprosthesis for supporting walls of an anatomical canal, comprising:

at least two juxtaposed assemblies, each assembly comprising a plurality of longitudinally extending juxtaposed ribs and a plurality of pairs of transverse strands interconnecting said ribs, said ribs in each assembly including an intermediate rib and a pair of external ribs spaced from and extending along opposite sides of said intermediate rib, said transverse strands in each assembly interconnecting said intermediate and external ribs and each pair of transverse strands forming a V shape, all of said V shapes being oriented in a same longitudinal direction with respect to said intermediate rib, said transverse strands being flexible and elastic, wherein said at least two assemblies are juxtaposed and connected together to form an open-ended cylinder with generally parallelogram-shaped openings defined by each pair of adjacent ribs and each pair of adjacent transverse strands, said cylinder being narrowed for insertion into the canal by applying tension in opposite longitudinal directions to an adjacent pair of said longitudinal ribs.

2. An endoprosthesis according to claim 1, wherein said assembly is made of an elastic material selected from the group consisting of elastic metals, elastic metal alloys and plastics.

3. An endoprosthesis according to claim 1, Wherein each of said external ribs is provided at its ends with orifices, which make it possible to fasten said assembly to an application device.

4. An application device for the endoprosthesis according to claim 3, comprising two concentric cylinders, each of said cylinders being provided at its distal end with spurs in equal number for engaging said orifices of said assembly to position said assembly on said device, and said cylinders being adapted to slide one on the other so as to stretch and flatten the prosthesis in order to position the prosthesis in the canal in which it is to be installed.

5. An endoprosthesis according to claim 1, wherein a longitudinal extension of each said V-shape in response to said tension is substantially equal to a longitudinal extension of said endoprosthesis as a whole.

6. An endoprosthesis according to claim 1, wherein the intermediate rib of each of the assemblies is laterally spaced from each of the respective external ribs by equal predetermined distances, such that the transverse strands form uniform V-shapes with respect to said intermediate rib, thereby permitting uniform expansion and compression of the endoprosthesis along its length in response to said tension applied to said adjacent pair of longitudinal ribs.

7. An endoprosthesis according to claim 6, wherein a longitudinal extension of each said V-shape in response to said tension is substantially equal to a longitudinal extension of said endoprosthesis as a whole.

8. An endoprosthesis according to claim 1, wherein each of the external ribs is provided at its ends with orifices for fastening the endoprosthesis to an application device.

9. An autoexpandable endoprosthesis for supporting the walls of an anatomic channel, the endoprosthesis having opposed ends, a longitudinal axis and a substantially openworked cylindrical shape forming an internal lumen;

the endoprosthesis having a compressed configuration, wherein the endoprosthesis is compressed for insertion into the canal and the internal lumen is of a relatively small diameter, and an expanded configuration in which the endoprosthesis is in a normally expanded condition with the internal lumen having a relatively large diameter, the endoprosthesis comprising:

a plurality of longitudinal external ribs having opposed ends and being distributed in parallel about the longitudinal axis of the endoprosthesis;

a plurality of longitudinal intermediate ribs having opposed ends and being distributed in parallel about the longitudinal axis of the endoprosthesis, each of the intermediate ribs being disposed between two of the external ribs, the intermediate ribs being longitudinally spaced from the respective external ribs by an equal predetermined distance, wherein at each end of the endoprosthesis the ends of the intermediate ribs are separated from the ends of the respective external ribs by the predetermined distance;

a plurality of rings distributed along the longitudinal axis of the endoprosthesis for connecting the external and intermediate ribs together, each of the rings being comprised of a plurality of pairs of transverse strands, each of the pairs of strands forming a V-shape having a summit which is connected to the respective intermediate rib and opposed ends which are connected to the respective external ribs elements, the V-shapes of each pair of strands of each ring being oriented in the same direction, the intermediate ribs and the strands attached thereto forming a herringbone pattern, the compressed configuration being obtained by the longitudinal tension of neighboring external ribs in opposite directions with respect to the intermediate ribs, in the axial direction of the endoprosthesis.

10. An endoprosthesis according to claim 9, wherein each said rib and strand is made of an elastic material selected from the group consisting of elastic metals, elastic metal alloys and plastics.

11. An endoprosthesis according to claim 10, wherein each said rib and strand has elasticity due to said elastic material such that said cylinder expands from said narrowed condition when said applied tension is released.

12. An endoprosthesis according to claim 9, wherein a longitudinal extension of each said V-shape in response to said tension is substantially equal to a longitudinal extension of said endoprosthesis as a whole.

13. An endoprosthesis according to claim 9, wherein said pairs of transverse strands form uniform V-shapes with respect to a corresponding said intermediate rib, thereby permitting uniform expansion and compression of the endoprosthesis along its length in response to said tension applied to said adjacent pair of longitudinal ribs.

14. An endoprosthesis according to claim 13, wherein a longitudinal extension of each said V-shape in response to said tension is substantially equal to a longitudinal extension of said endoprosthesis as a whole.

15. An endoprosthesis according to claim 9, wherein each of the external ribs is provided at its ends with orifices for fastening the endoprosthesis to an application device

* * * * *